United States Patent
Krebs et al.

(10) Patent No.: US 9,883,872 B2
(45) Date of Patent: Feb. 6, 2018

(54) ADJUSTABLE REAMING DEVICE HAVING A DISCRETELY POSITIONABLE STOP ELEMENT

(71) Applicant: Zimmer, Inc., Warsaw, IN (US)

(72) Inventors: Robert D. Krebs, Warsaw, IN (US); Sarah Ann Paro, Winona Lake, IN (US); Paul Borries, Columbia City, IN (US); Lisa Carlin, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 375 days.

(21) Appl. No.: 14/807,032

(22) Filed: Jul. 23, 2015

(65) Prior Publication Data

US 2016/0051266 A1 Feb. 25, 2016

Related U.S. Application Data

(60) Provisional application No. 62/039,499, filed on Aug. 20, 2014.

(51) Int. Cl.
*A61B 17/00* (2006.01)
*A61B 17/16* (2006.01)
*A61B 17/17* (2006.01)
*A61B 90/00* (2016.01)

(52) U.S. Cl.
CPC ........ *A61B 17/1617* (2013.01); *A61B 17/164* (2013.01); *A61B 17/175* (2013.01); *A61B 2090/033* (2016.02)

(58) Field of Classification Search
CPC combination set(s) only.
See application file for complete search history.

(56) References Cited

U.S. PATENT DOCUMENTS

2010/0069907 A1* 3/2010 Sidebotham ....... A61B 17/1617
606/80

* cited by examiner

*Primary Examiner* — Sameh Boles
(74) *Attorney, Agent, or Firm* — Schwegman Lundberg & Woessner, P.A.

(57) ABSTRACT

An adjustable reaming device can include a proximal reamer and a positionable element. The positionable element removably attaches to the proximal reamer at one of a plurality of discrete longitudinal locations along the proximal reamer. A distal end of the positionable element forms a stop, which can contact a proximal end of a distal reamer and thereby limit distal motion of the proximal reamer with respect to the distal reamer. When the distal reamer is in contact with the positionable element, the distal reamer and proximal reamer are longitudinally offset by a one of a plurality of specified offsets. In some examples, the specified offsets correspond to a plurality of specified, discrete lengths for which implantable femoral stems are available.

12 Claims, 11 Drawing Sheets

ADJUSTABLE REAMING DEVICE HAVING A DISCRETELY POSITIONABLE STOP ELEMENT

CLAIM OF PRIORITY

This application claims the benefit of U.S. Provisional Patent Application Ser. No. 62/039,499, filed on Aug. 20, 2014, the benefit of priority of which is claimed hereby, and which is incorporated by reference herein in its entirety.

BACKGROUND

Some surgical hip replacement procedures ream a portion of a femur to accommodate an implantable femoral stem. In many cases, the implantable femoral stems are available only in discrete sizes, with stem lengths that have one of a plurality of discrete values. In these cases, a surgeon can select an implantable femoral stem having a stem length that most closely matches an anatomy of a patient.

Once the femoral stem is selected, a surgeon can ream the femur to accept the femoral stem. The reamed portion can be sized and shaped to accommodate the selected femoral stem. In many cases, the surgeon can use a distal reamer to form the bottommost (distal) portion of the reamed portion, and use an additional proximal reamer to shape an upper (proximal) portion of the reamed portion.

For these cases, the surgeon can use one or more spacers to ensure that the proximal and distal reamers are longitudinally offset by a distance that corresponds to one of the available stem lengths. In some examples, the spacers can be tubular spacer sleeves having suitable lengths, which can extend distally from the proximal reamer and can fit over the distal reamer.

OVERVIEW

An adjustable reaming device can include a proximal reamer and a positionable element. The positionable element removably attaches to the proximal reamer at one of a plurality of discrete longitudinal locations along the proximal reamer. A distal end of the positionable element forms a stop, which can contact a proximal end of a distal reamer or another type of guide rod. The stop thereby limits distal motion of the proximal reamer with respect to the distal reamer. When the distal reamer is in contact with the positionable element, the distal reamer and proximal reamer are longitudinally offset by a one of a plurality of specified offsets. In some examples, the specified offsets correspond to a plurality of specified, discrete lengths for which implantable femoral stems are available.

In some examples, an adjustable reaming device can include a longitudinally-elongated proximal reamer. A distal end of the proximal reamer can define a distal opening into an interior of the proximal reamer. The distal end of the proximal reamer can include at least one cutting flute surrounding the distal opening. The adjustable reaming device can further include a positionable element, such as a stop element or a driver, disposed within the interior of the proximal reamer. A distal end of the positionable element can be configured to contact a proximal end of a distal reamer insertable into the distal opening of the proximal reamer. The positionable element can be switchable between an unlocked state, in which the positionable element is longitudinally positionable with respect to the proximal reamer, and a locked state, in which the positionable element is locked to the proximal reamer at one of a plurality of discrete, specified longitudinal locations along the proximal reamer.

A method for adjusting a reaming device can include providing a longitudinally-elongated proximal reamer. A distal end of the proximal reamer can define a distal opening into an interior of the proximal reamer. The method can further include positioning a positionable element longitudinally within the proximal reamer. A distal end of the positionable element can be configured to abut a distal reamer insertable into the distal opening, thereby limiting longitudinal motion of the proximal reamer in the distal direction, with respect to the distal reamer, but not in the proximal direction, with respect to the distal reamer. The method can further include locking the positionable element to the proximal reamer at one of a plurality of discrete, specified longitudinal locations along the proximal reamer.

This Overview is intended to provide examples of the present patent document. It is not intended to provide an exclusive or exhaustive explanation of the invention. The Detailed Description below is included to provide further information about the present adjustable reaming device.

BRIEF DESCRIPTION OF THE DRAWINGS

In the drawings, which are not necessarily drawn to scale, like numerals describe similar components in different views. The drawings illustrate generally, by way of example, but not by way of limitation, various embodiments discussed in the present patent document.

DETAILED DESCRIPTION

FIGS. 1A and 1B are schematic views of an example of a positionable element 104 that is repositionable within a longitudinally-elongated proximal reamer 102 at a plurality of discrete, specified longitudinal locations 108A-D along the proximal reamer 102. In the configuration shown in FIGS. 1A and 1B, the positionable element 104 is positioned at longitudinal location 108C.

A distal end of the proximal reamer 102 can define a distal opening into an interior of the proximal reamer 102. The positionable element 104 can be positioned longitudinally within the proximal reamer 102. A distal end of the positionable element 104 can be configured to abut a distal reamer 106 insertable into the distal opening, thereby limiting longitudinal motion of the proximal reamer 102 in the distal direction, with respect to the distal reamer 106, but not in the proximal direction, with respect to the distal reamer 106. Distal reamers are surgical instruments that are well-known to one of ordinary skill in the art.

The positionable element 104 can be locked to the proximal reamer 102 at each of the plurality of discrete, specified longitudinal locations 108A-D along the proximal reamer 102. In some examples, the positionable element 104 can be unlocked from the proximal reamer 102, can be repositioned longitudinally within the proximal reamer 102 to another of the discrete, specified longitudinal locations 108A-D, and can be locked once again to the proximal reamer 102.

FIGS. 2-10 show various configurations of the proximal reamer and positionable element, as well as various examples of the mechanisms with which they can be locked to each other and unlocked from each other. In some examples, such as the examples of FIGS. 2-5, the positionable element is a stop element. In some examples, such as the examples of FIGS. 6-10, the positionable element is a driver. Other suitable proximal reamers, positionable elements, and configurations can also be used.

Figure 2:
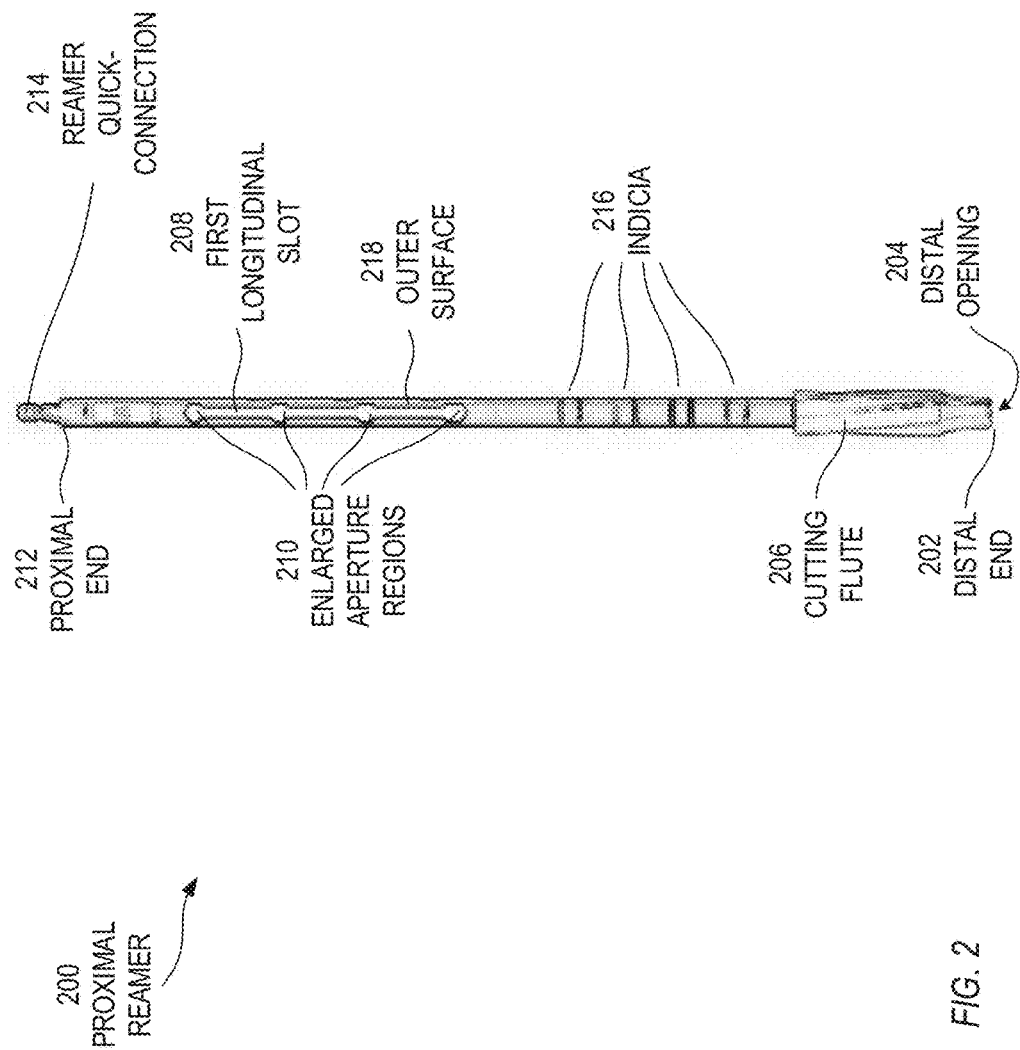
FIG. 2 is a side view of an example of a proximal reamer.

FIG. 2 is a side view of an example of a longitudinally-elongated proximal reamer 200. The configuration of FIG. 2 is but one example; other suitable proximal reamers can also be used.

A distal end 202 of the proximal reamer 200 can define a distal opening 204 into an interior of the proximal reamer 200. The distal end 202 of the proximal reamer 200 can include at least one cutting flute 206 surrounding the distal opening 204. The cutting flute 206 can include one or more helical blades on its exterior surface. The blade or blades can have a shape and geometry that can vary with the particular surgical application.

The proximal reamer 200 can further define a first longitudinal slot 208 formed in an outer surface 218 of the reamer. In some examples, the first longitudinal slot 208 can extend fully along the longitudinal extent of the proximal reamer 200. In other examples, the first longitudinal slot 208 can terminate proximal of the distal end 202 of the proximal reamer, and/or can terminate distal of a proximal end 212 of the proximal reamer 200.

The proximal reamer 200 can further define a first plurality of enlarged aperture regions 210 disposed along the first longitudinal slot 208. In some examples, the enlarged aperture regions 210 can be circular; in other examples, other suitable shapes can be used. In some examples, an enlarged aperture region 210 can be disposed at one longitudinal end of the first longitudinal slot 208. In some examples, two enlarged aperture regions 210 are disposed at opposite longitudinal ends of the first longitudinal slot 208.

In some examples, the proximal reamer 200 can include first and second longitudinal slots formed on opposite sides of the proximal reamer 200. In these examples, the proximal reamer 200 can further define first and second pluralities of enlarged aperture regions along the first and second longitudinal slots, respectively. In these examples, each enlarged aperture region in the first plurality can be positioned at the same location as a corresponding enlarged aperture region in the second plurality. In other examples, the proximal reamer can include more than two longitudinal slots, located circumferentially around the proximal reamer. In these examples, the enlarged aperture regions can be positioned at the same longitudinal locations along the longitudinal slots.

The proximal reamer 200 can further include a reamer quick-connection 214 positioned on the proximal end 212 of the proximal reamer 200. The quick-connection 214 can be a Hudson style, or any other suitable configuration.

The proximal reamer 200 can further include indicia 216. The indicia can include one or more of colored markings, colored bands, letters, and numbers, all of which can provide a visual indication of a particular configuration of proximal reamer 200 and/or a particular longitudinal location along the proximal reamer 200.

Figure 3:
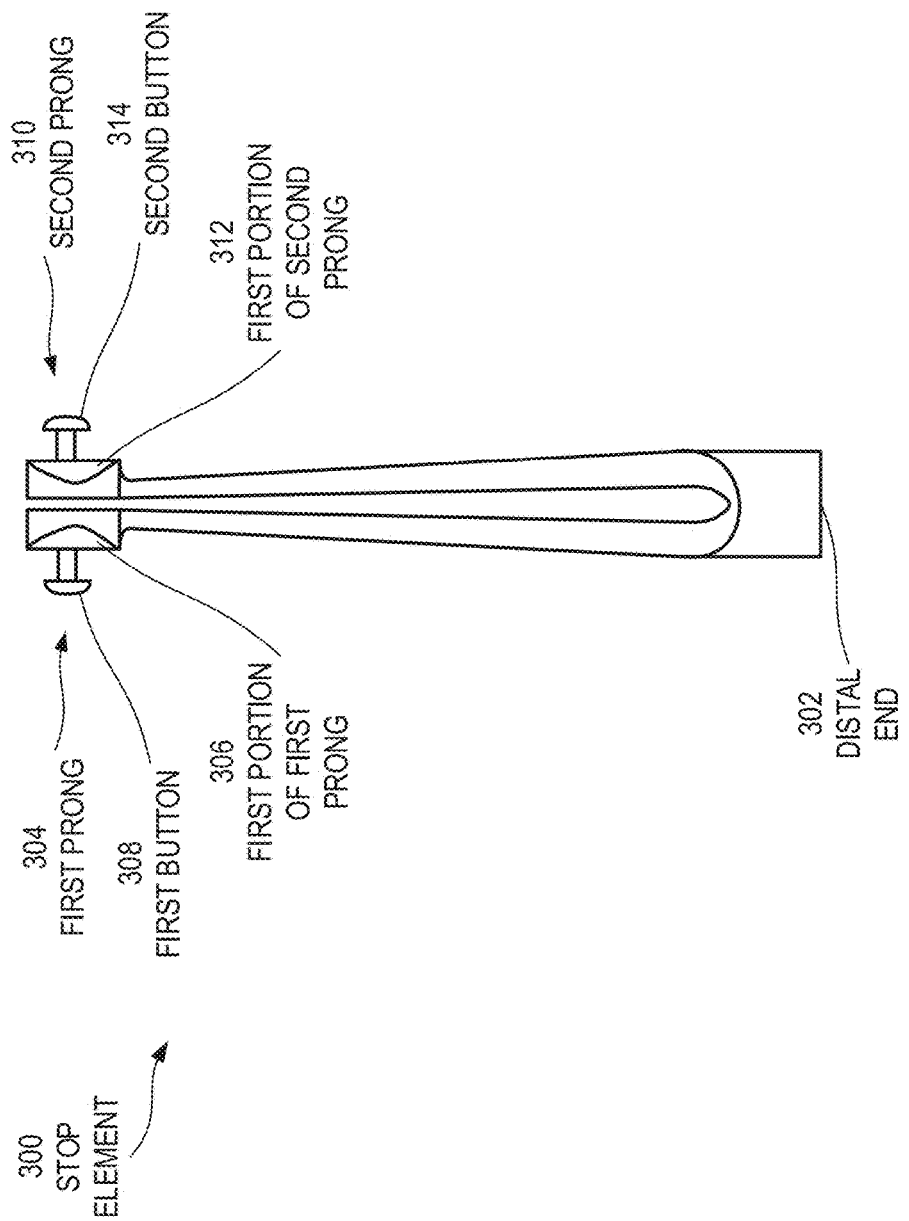
FIG. 3 is a side view of an example of a stop element.

FIG. 3 is a side view of an example of a stop element 300. During use, the stop element 300 can be disposed within the interior of the proximal reamer. The stop element 300 can be switchable between an unlocked state, in which the stop element 300 is longitudinally positionable with respect to the proximal reamer (for example, proximal reamer 200 of FIG. 2), and a locked state, in which the stop element 300 is locked to or engages the proximal reamer (200; FIG. 2) at one of a plurality of discrete, specified longitudinal locations along the proximal reamer (200; FIG. 2). The configuration of FIG. 3 is but one example; other suitable stop elements can also be used.

Figure 1:
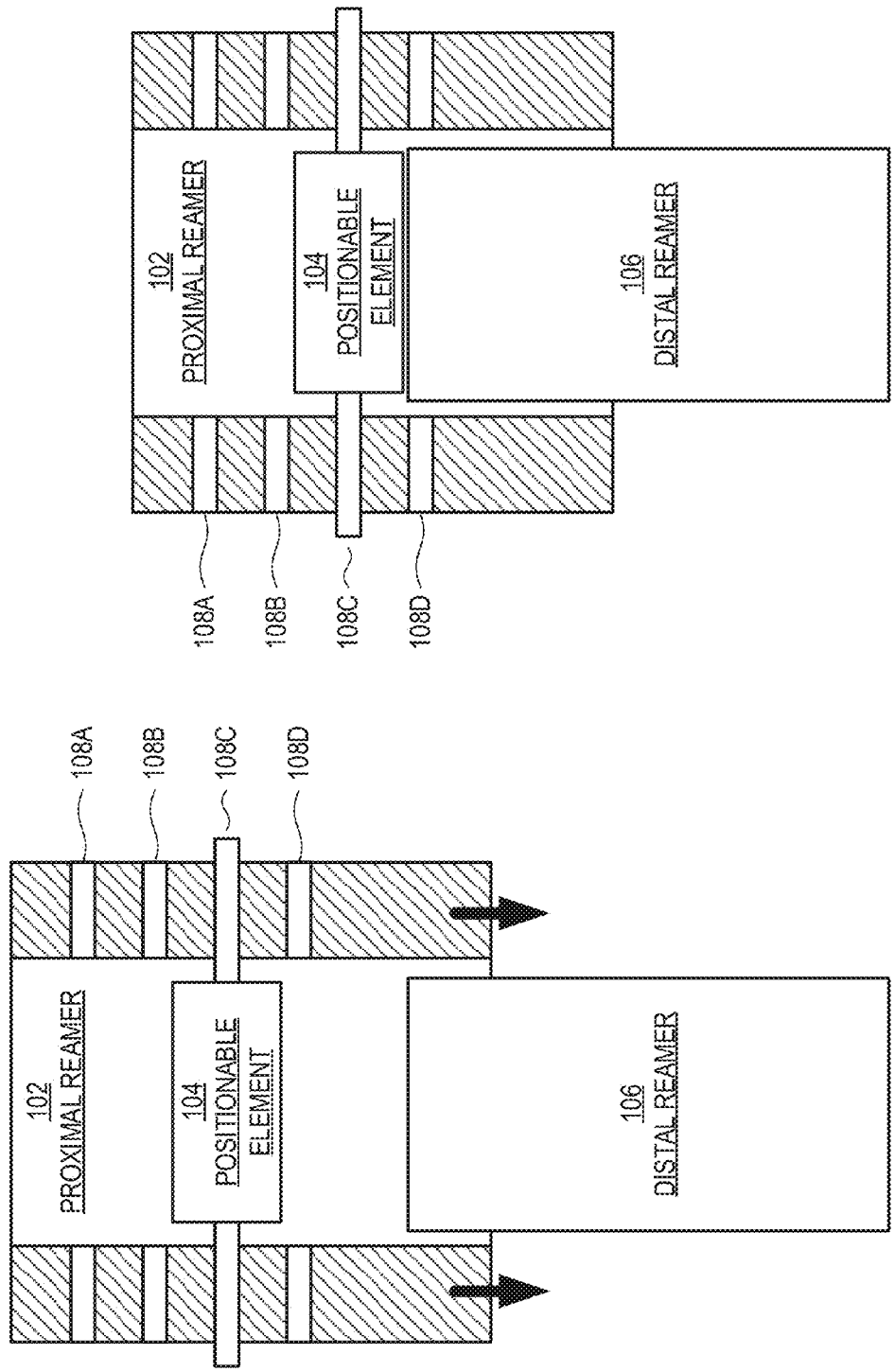
FIGS. 1A and 1B are schematic views of an example of a positionable element that is repositionable within a longitudinally-elongated proximal reamer at a plurality of discrete, specified longitudinal locations along the proximal reamer.

A distal end 302 of the stop element 300 can be configured to contact a proximal end of a distal reamer insertable into the distal opening of the proximal reamer (for example, distal reamer 106 of FIG. 1). In some examples, the distal end 302 can be flat and perpendicular to a longitudinal axis of the proximal reamer 200. In some examples, the distal end 302 can be convex. In some examples, the distal end 302 can be rotationally symmetric with respect to the longitudinal axis of the proximal reamer 200. For these examples, the stop element 300 can be rotationally decoupled from the distal reamer. In other examples, the distal end 302 can include one or more features that can rotationally couple the stop element 300 to the distal reamer.

The stop element 300 can include a first prong 304 biased to extend radially outward from within the proximal reamer. A first portion 306 of the first prong 304 can be sized larger than a circumferential diameter of the first longitudinal slot (208; FIG. 2) and smaller than the enlarged aperture regions (210; FIG. 2) in the first plurality. When the stop element 300 switches from the unlocked state to the locked state, the first portion 306 of the first prong 304 snaps into or engages one of the enlarged aperture regions (210; FIG. 2) in the first plurality, thereby locking the stop element 300 to the proximal reamer (200; FIG. 2).

The stop element 300 can include a first button 308 disposed on the first prong 304 and configured to transmit radially-inward force to the first prong. When the stop element 300 is locked to the proximal reamer (200; FIG. 2), the radially-inward force can radially compress the stop element 300, thereby unlocking the stop element 300 from the proximal reamer (200; FIG. 2). When the stop element 300 is in the unlocked state, a user can apply a longitudinal force to the first button 308, which can longitudinally translate the stop element 300 with respect to the proximal reamer (200; FIG. 2).

In some examples, the stop element 300 can include first and second buttons 308, 314 disposed on the first and second prongs 304, 310, respectively, and configured to transmit radially-inward force to the first and second prongs 304, 310, so that when the stop element 300 is locked to the proximal reamer, the radially-inward force can radially compress the stop element 300, thereby unlocking the stop element 300 from the proximal reamer.

In some examples, such as the example of FIG. 3, the stop element can be U-shaped. In some examples, a bottom of the U-shape can be configured to abut the distal reamer. In some examples, a top of the U-shape can include the first and second prongs 304, 310.

Figure 4:
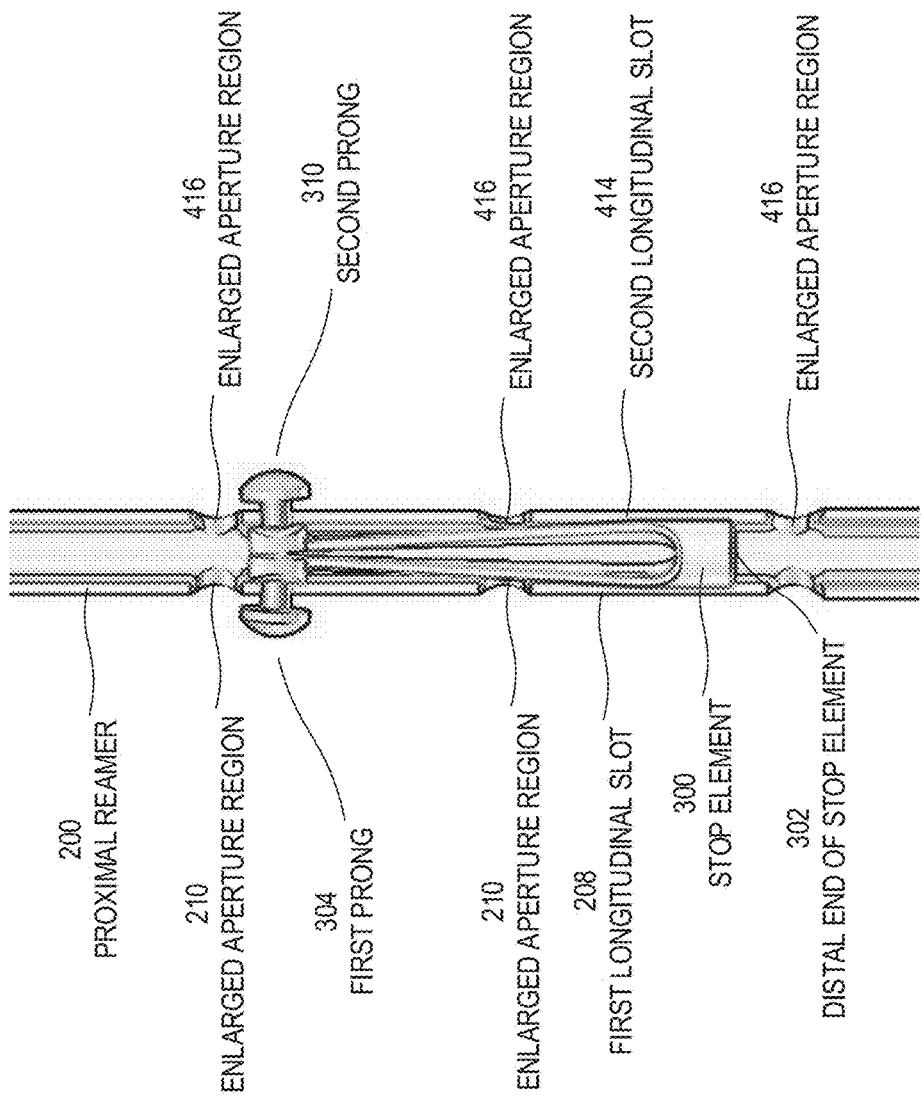
FIG. 4 is a cross-sectional view of a portion of an example of a stop element disposed within a proximal reamer.

FIG. 4 is a cross-sectional view of a portion of the stop element 300 of FIG. 3, disposed within the proximal reamer 200.

In some examples, the stop element 300 can include first and second prongs 304, 310 biased to extend radially outward in opposite directions from within the proximal reamer 200. A first portion of the first prong 304 can be sized larger than a circumferential diameter of the first longitudinal slot 208 and smaller than the enlarged aperture regions 210 in the first plurality. Likewise, a first portion of the second prong 310 can be sized larger than a circumferential diameter of a second longitudinal slot 414 and smaller than enlarged aperture regions 416 in the second plurality. When the stop element 300 switches from the unlocked state to the locked state, the first portions of the first and second prongs 304, 310 snap into corresponding enlarged aperture regions 210, 416 in the first and second pluralities, thereby locking the stop element 300 to the proximal reamer 200.

Figure 5:
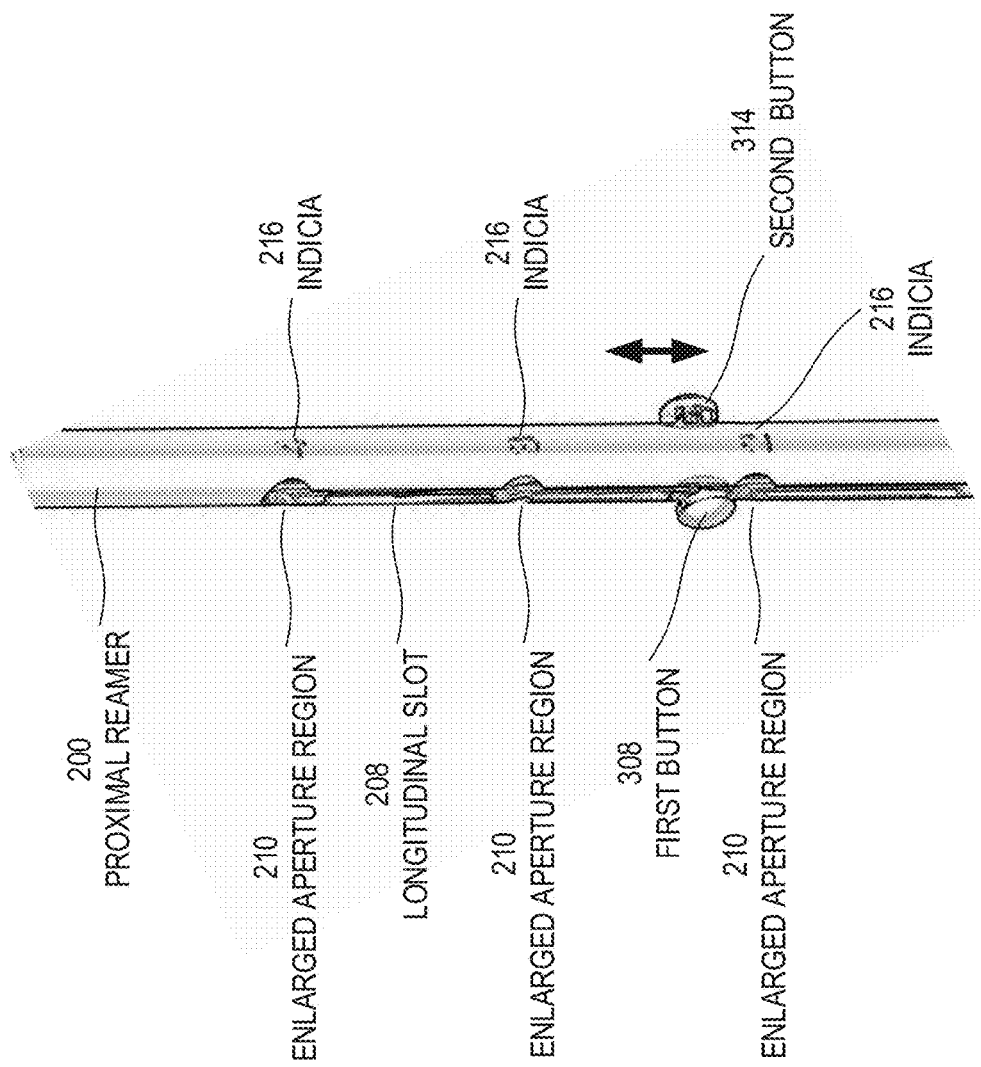
FIG. 5 is a perspective view of an example of a stop element disposed within a proximal reamer.

FIG. 5 is a perspective view of an example of the stop element 300 disposed within the proximal reamer 200. The configuration of FIG. 5 is but one example; other suitable configurations can also be used.

When the stop element 300 is in the unlocked state, the first button 308, or the first and second buttons 308, 314, can longitudinally translate the stop element with respect to the proximal reamer 200. The buttons can be used to unlock the stop element from a first opposing pair of enlarged aperture regions (by pressing the buttons together, thereby radially compressing the stop element), reposition the stop element along opposing longitudinal slots to a second opposing pair of enlarged aperture regions, and lock the stop element (by allowing the prongs to snap radially outward through the second opposing pair of enlarged aperture regions, thereby radially expanding the stop element).

The proximal reamer 200 can optionally include indicia 216, such as one or more letters, one or more numbers, one or more patterns, one or more colors, and others. The indicia 216 can provide visual identification of the corresponding enlarged aperture region 210.

In some examples, an adjustable reaming device can include the proximal reamer and the stop element. In other examples, the adjustable reaming device can include the proximal reamer, the stop element, and a longitudinally-elongated distal reamer, such as 106 (FIG. 1). The distal reamer can be insertable into the distal opening of the proximal reamer. The distal reamer can be rotationally uncoupled from the proximal reamer. The stop element limits longitudinal motion of the proximal reamer in the distal direction, with respect to the distal reamer, but not in the proximal direction, with respect to the distal reamer.

In the examples of FIGS. 2-5, a positionable element locks to a proximal reamer by using outwardly-biased prongs that snap radially outward into enlarged aperture regions when the positionable element is suitable positioned along the proximal reamer. To unlock the positionable element from the proximal reamer, a user forces a pair of buttons against each other, thereby forcing the prongs radially inward and releasing them from the enlarged aperture regions. This is but one example of a locking/unlocking mechanism.

The examples of FIGS. 6-10 can use a locking/unlocking mechanism in which a user locks the positionable element to the proximal reamer by pivoting the positionable element about its longitudinal axis, with respect to the proximal reamer. As the user pivots these elements with respect to each other, an outward-extending prong can travel along a circumferential slot. The end of the circumferential slot can include a spring mechanism that locks the prong to the end of the slot. The user can unlock the positionable element from the proximal reamer by pivoting the elements in the opposite direction with a torque that exceeds a specified threshold, thereby overcoming the spring mechanism. The examples of FIGS. 6-10 are but one locking/unlocking mechanism; other suitable mechanisms can also be used.

Figure 6:
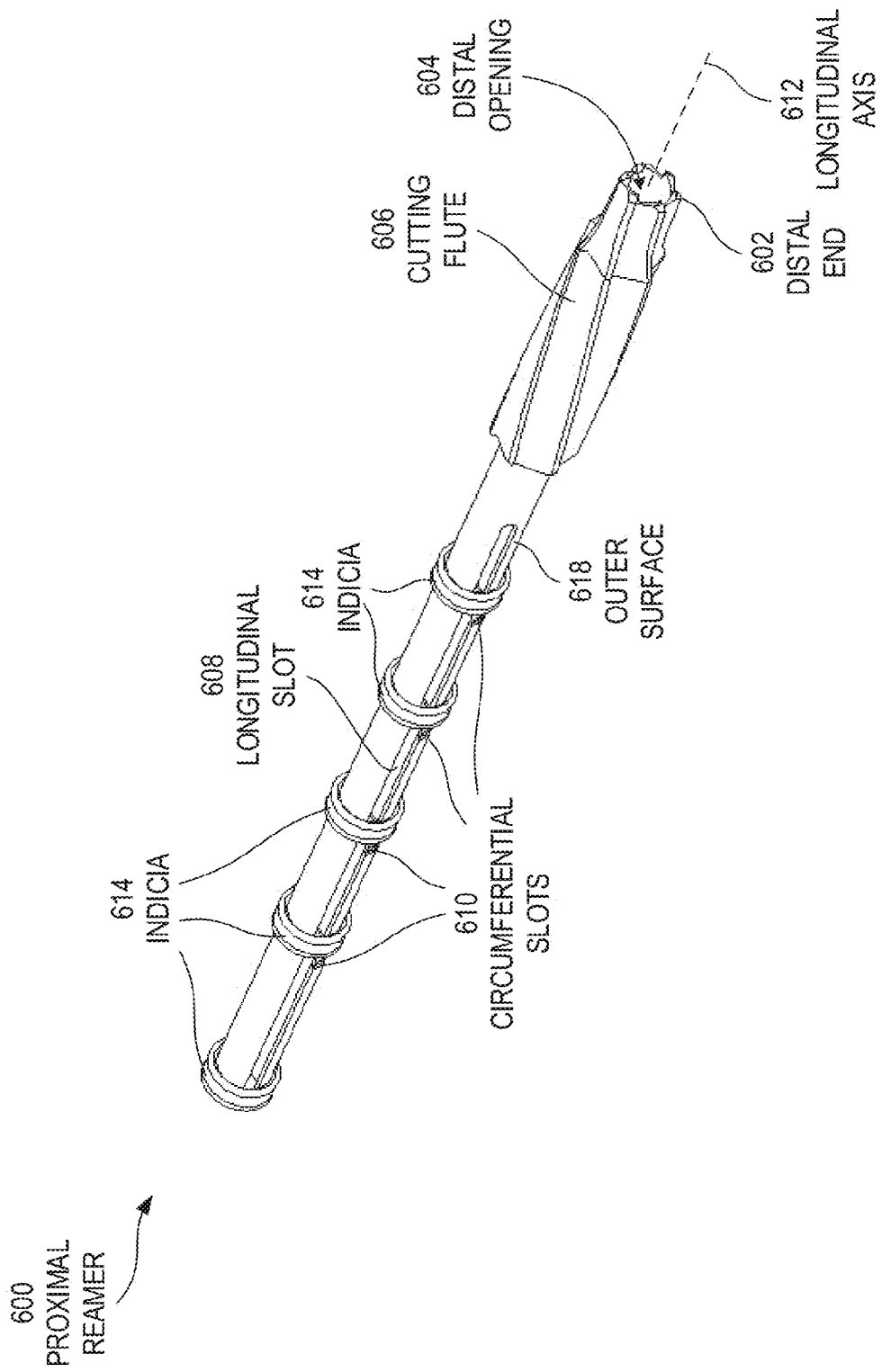
FIG. 6 is a perspective view of another example of a proximal reamer.

FIG. 6 is a perspective view of another example of a proximal reamer 600. The configuration of FIG. 6 is but one example; other suitable proximal reamers can also be used.

A distal end 602 of the proximal reamer 600 can define a distal opening 604 into an interior of the proximal reamer 600. The distal end 602 of the proximal reamer 600 can include at least one cutting flute 606 surrounding the distal opening 604.

The proximal reamer 600 can define at least one longitudinal slot 608 formed in an outer surface 618 of the reamer, as well as a plurality of circumferential slots 610 therethrough. Each circumferential slot 610 in the plurality can have a first end that is connected to the longitudinal slot 608. Each circumferential slot 610 in the plurality can have a second end that includes a spring mechanism (discussed below and shown in FIGS. 9 and 10). The proximal reamer 600 can be elongated along longitudinal axis 612.

The proximal reamer 600 can also include indicia 614, which can provide visual identification for each of the circumferential slots 610.

Figure 7:
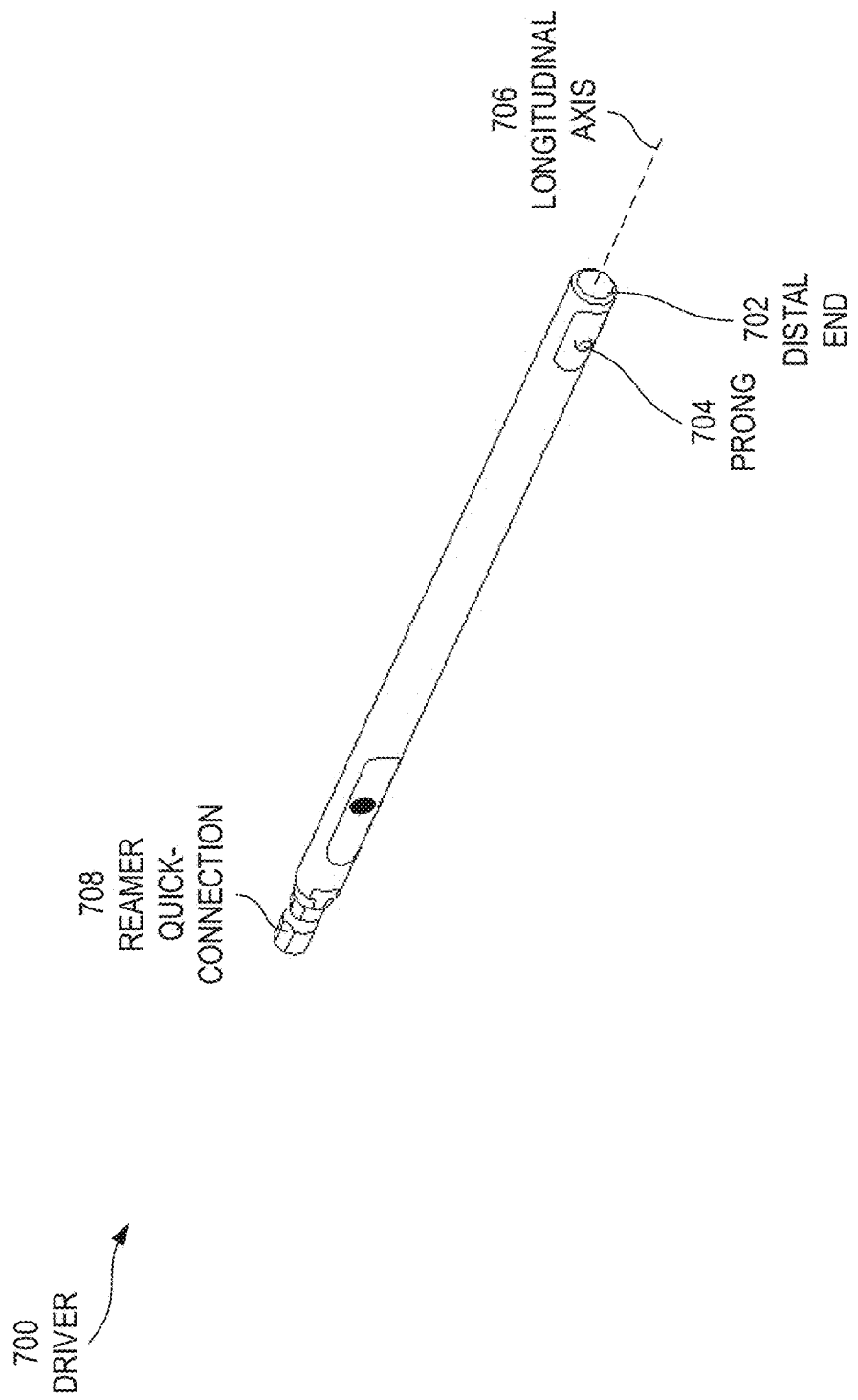
FIG. 7 is a perspective view of an example of a driver.

FIG. 7 is a perspective view of an example of a driver 700. During use, the driver 700 can be partially or fully disposed within the interior of the proximal reamer (600; FIG. 6). The driver 700 can be elongated along longitudinal axis 706.

A distal end 702 of the driver 700 can be configured to contact a proximal end of a distal reamer insertable into the distal opening (604; FIG. 6) of the proximal reamer (600; FIG. 6). The driver 700 can include a prong 704 extending radially outward from within the proximal reamer (600; FIG. 6). The prong 704 can be sized to fit within the longitudinal slot (608; FIG. 6) and the circumferential slots (610; FIG. 6) in the plurality. The driver 700 can include a reamer quick-connection 708 positioned on a proximal end of the driver.

Figure 8:
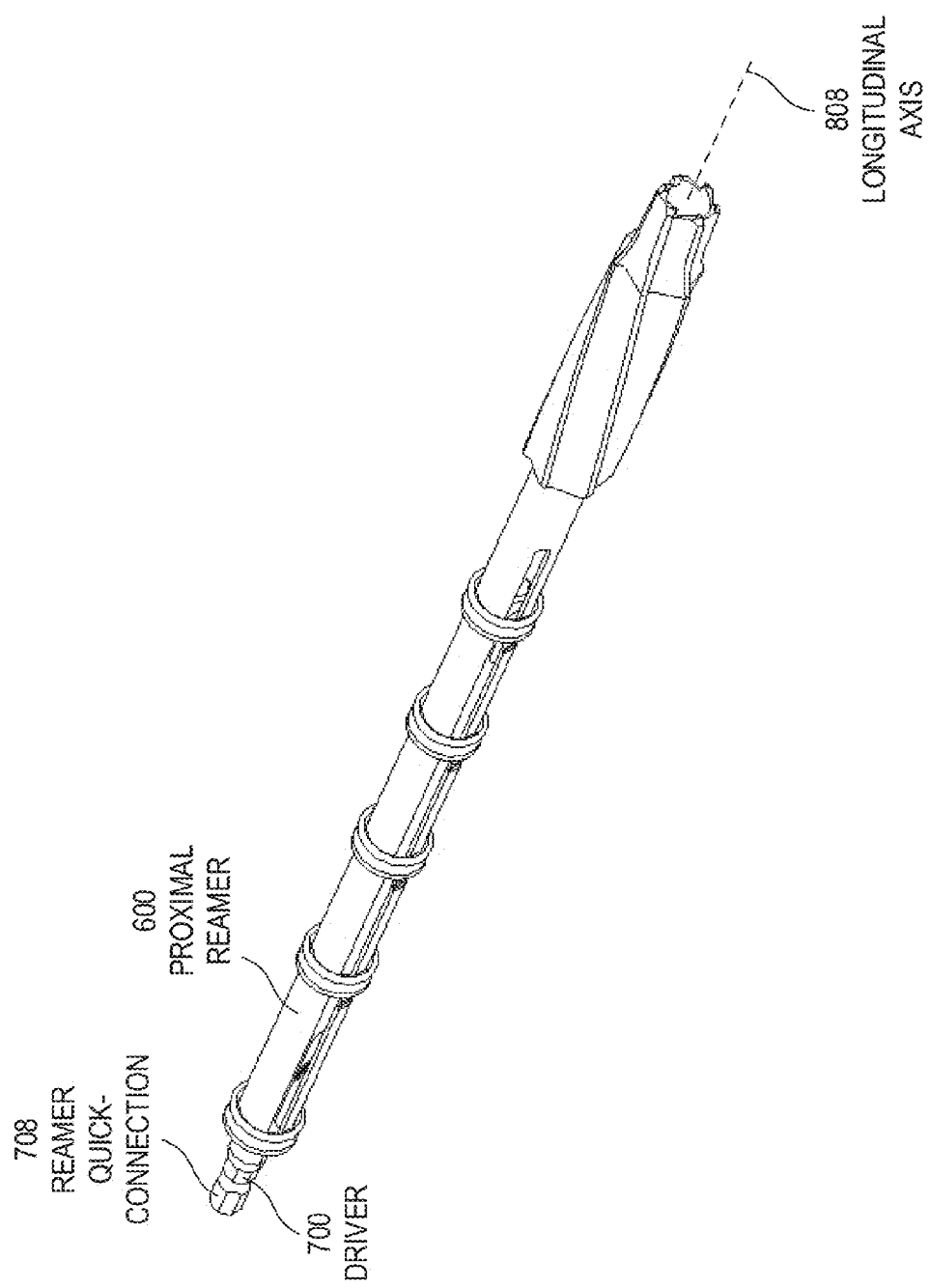
FIG. 8 is a perspective view of an example of an adjustable reaming device, having a driver disposed within a proximal reamer.

FIG. 8 is a perspective view of an example of the proximal reamer 600 of FIG. 6 having the driver 700 of FIG. 7 disposed therein. During use, the reamer quick-connection 708 on the driver 700 can extend proximally beyond a proximal end of the proximal reamer 600. During use, the longitudinal axes of the driver 700 and the proximal reamer 600 can coincide, along longitudinal axis 808.

During use, the driver 700 can be switched between an unlocked state, in which the driver 700 is longitudinally positionable with respect to the proximal reamer 600, and a locked state, in which the driver 700 is locked to the proximal reamer 600 at one of a plurality of discrete, specified longitudinal locations along the proximal reamer 600.

When the driver 700 switches from the unlocked state to the locked state, the driver 700 can be positioned longitudinally so that the prong (704; FIG. 7) aligns with one of the circumferential slots (610; FIG. 6), then the driver 700 is rotated about longitudinal axis 808 so that the prong (704;

FIG. 7) traverses the circumferential slot (610; FIG. 6) and engages the spring mechanism (discussed below and shown in FIGS. 9 and 10).

Figure 9:
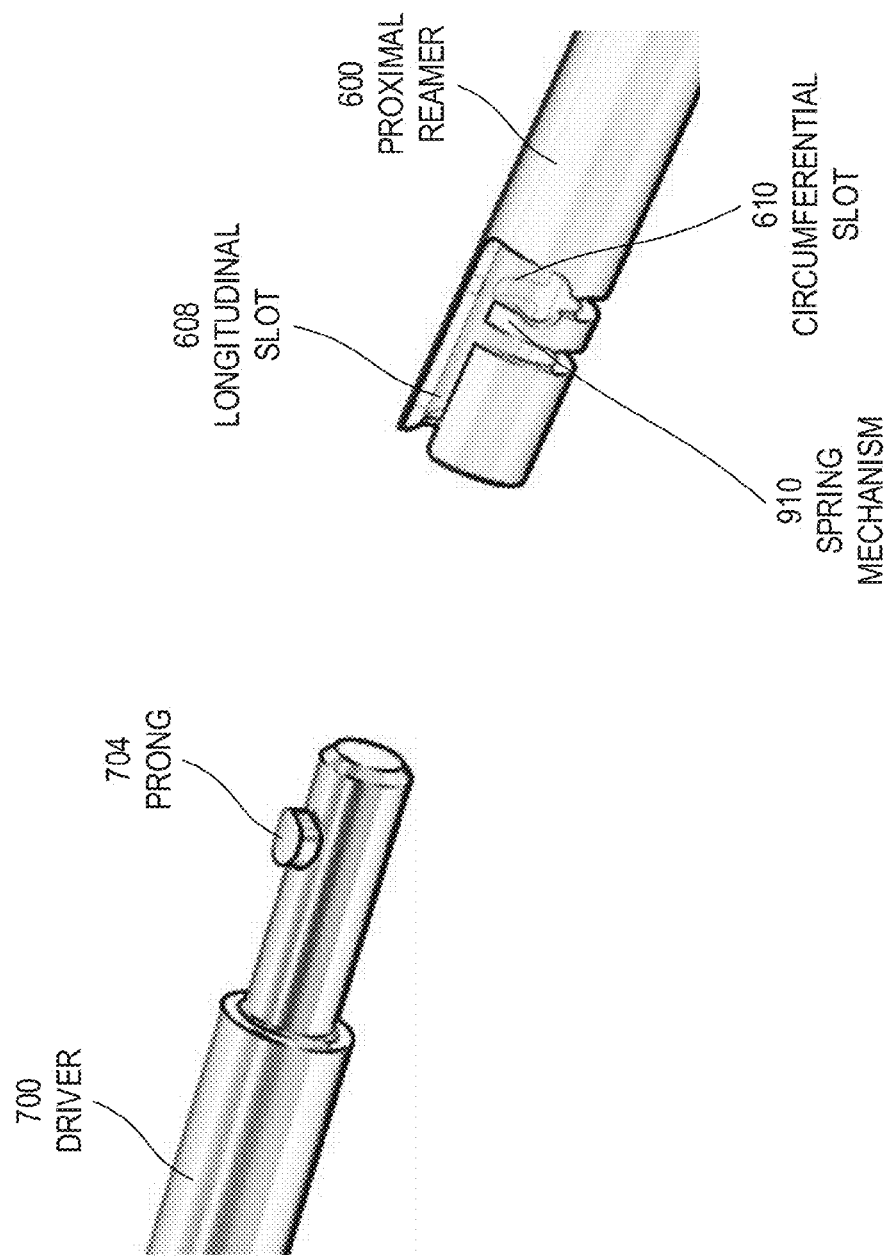
FIG. 9 is a perspective view of an example of a portion of a driver, separated from an example of a portion of a proximal reamer.

FIG. 9 more clearly shows the prong 704 on the driver 700, and the longitudinal slot 608, circumferential slot 610, and spring mechanism 910 on the proximal reamer 600. FIG. 9 omits some features from the driver 700 and the proximal reamer 600, in order to emphasize the prong 704, the longitudinal slot 608, the circumferential slot 610, and the spring mechanism 910.

The prong 704 can be sized to fit into both the longitudinal slot 608 and the circumferential slot 610. In particular, the prong 704 can have a circumferential diameter matched to a circumferential diameter of the longitudinal slot 608. The prong 704 can also have a longitudinal diameter matched to a longitudinal diameter of the circumferential slot 610.

Figure 10:
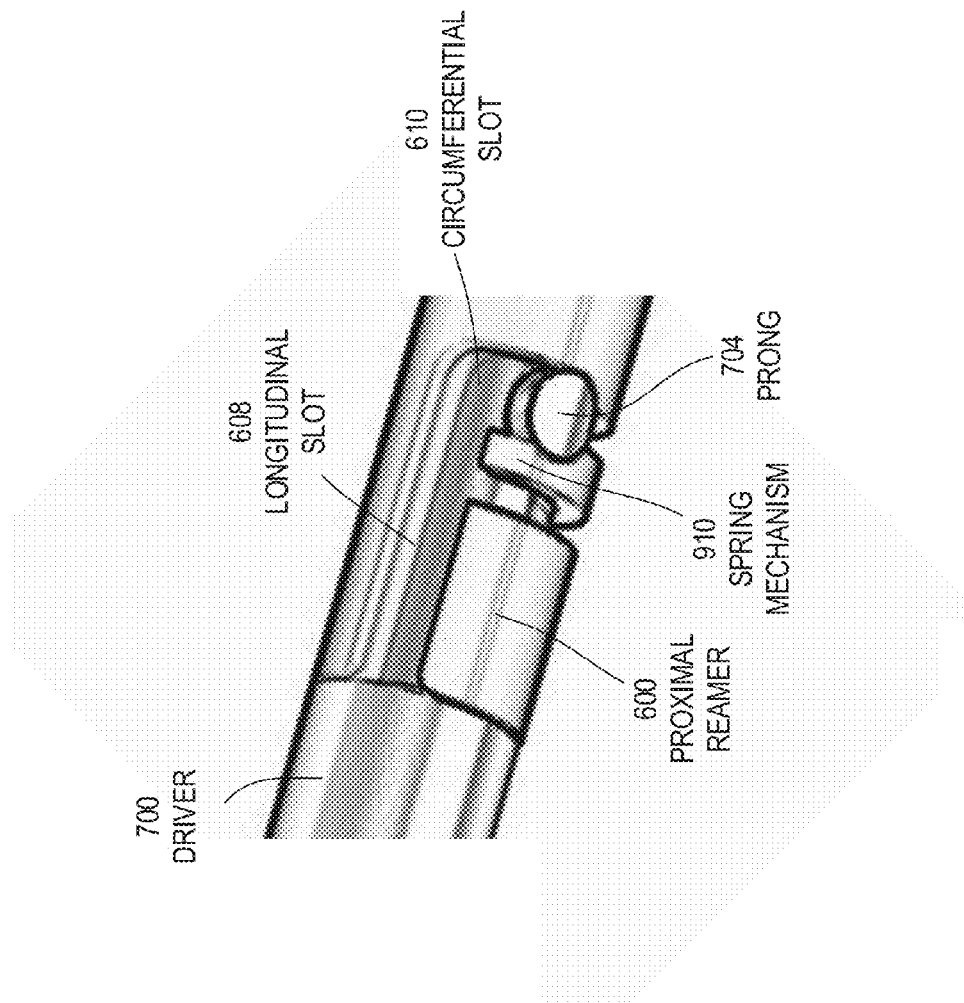
FIG. 10 is a perspective view of an example of the portion of the driver of FIG. 9, attached to the example of the portion of the proximal reamer of FIG. 9.

FIG. 10 is a perspective view of an example of the portion of the driver of FIG. 9, attached to the example of the portion of the proximal reamer of FIG. 9.

A user can engage the driver 700 and the proximal reamer 600 with a push-and-twist motion. The user can push, moving the prong 704 along the longitudinal 608 until the prong is longitudinally aligned with a one of the circumferential slots 610. The user can then twist, moving the prong 704 along the circumferential slot 610. At the end of the twisting motion, the prong 704 can engage the spring mechanism 910. The spring mechanism can engage when a torque or a force exceeds a particular engagement threshold. In the example of FIG. 9, the spring mechanism 910 includes a relatively thin spring member, which forms a wall of the circumferential slot 610. The spring member deforms when the prong 704 passes through the circumferential slot 610, and returns to an undeformed or relaxed state when the prong 704 reaches the end of the circumferential slot 610. The deformation of the spring member holds the prong 704 in place at the end of the circumferential slot 610. The spring mechanism 910 can be disengaged by applying the twisting motion in the opposite direction. The spring mechanism can disengage when the torque or force exceeds a particular disengagement threshold. In some examples, the disengagement threshold is the same as the engagement threshold.

In some examples, an adjustable reaming device can include the proximal reamer and the driver. In other examples, the adjustable reaming device can include the proximal reamer, the driver, and a longitudinally-elongated distal reamer, such as reamer 106 (FIG. 1). The distal reamer can be insertable into the distal opening of the proximal reamer. The distal reamer can be rotationally uncoupled from the proximal reamer. The configuration limits longitudinal motion of the proximal reamer in the distal direction, with respect to the distal reamer, but not in the proximal direction, with respect to the distal reamer.

Figure 11:
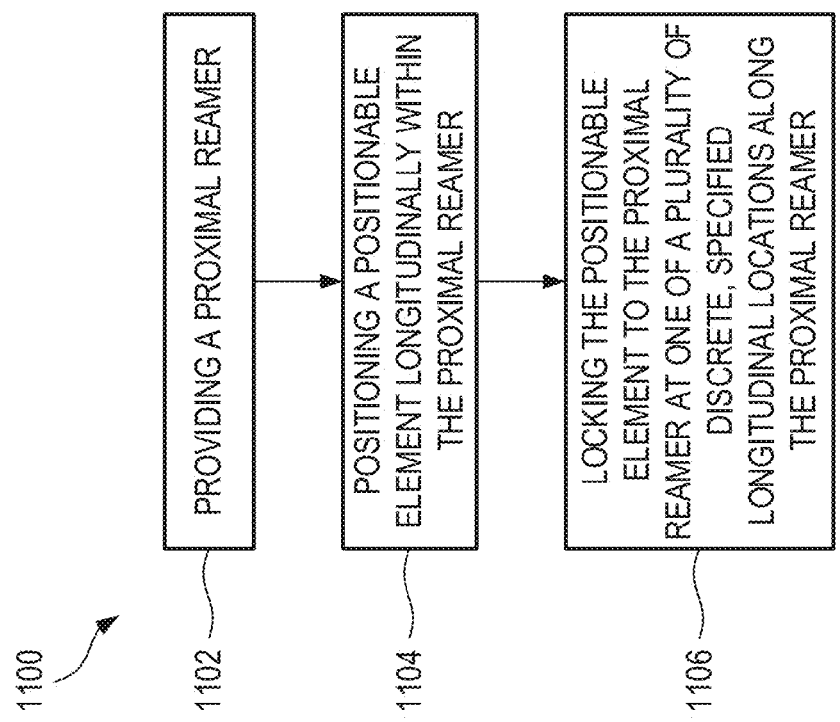
FIG. 11 is a flow chart of an example of a method for adjusting a reaming device.

FIG. 11 is a flow chart of an example of a method 1100 for adjusting a reaming device. The method can be executed by the adjustable reaming device of FIGS. 2-5, the adjustable reaming device of FIGS. 6-10, or another suitable adjustable reaming device. The method of FIG. 11 is but one example; other suitable examples can also be used.

At 1102, method 1100 provides a longitudinally-elongated proximal reamer, such as 200 (FIG. 2) or 600 (FIG. 6), or other suitable proximal reamers. A distal end of the proximal reamer can define a distal opening into an interior of the proximal reamer.

At 1104, method 1100 positions a positionable element longitudinally within the proximal reamer. In some examples, the positionable element can be a stop element, such as 300 (FIG. 3). In other examples, the positionable element can be a driver, such as 700 (FIG. 7). A distal end of the positionable element can be configured to abut a distal reamer insertable into the distal opening, thereby limiting longitudinal motion of the proximal reamer in the distal direction, with respect to the distal reamer, but not in the proximal direction, with respect to the distal reamer.

At 1106, method 1100 locks the positionable element to the proximal reamer at one of a plurality of discrete, specified longitudinal locations along the proximal reamer. The locations can be defined by the proximal reamer, the positionable element, or by both the proximal reamer and the positionable element.

In some examples, method 1100 can further include unlocking the positionable element from the proximal reamer. In some examples, method 1100 can further include repositioning the positionable element longitudinally within the proximal reamer to another of the discrete, specified longitudinal locations in the plurality. In some examples, method 1100 can further include locking the positionable element to the proximal reamer.

The following non-limiting list of examples can further illustrate the present adjustable reaming device and method for adjusting a reaming device.

In Example 1, an adjustable reaming device can comprise a longitudinally-elongated proximal reamer, a distal end of the proximal reamer defining a distal opening into an interior of the proximal reamer, the distal end of the proximal reamer including a cutting flute surrounding the distal opening; and a stop element disposed within the interior of the proximal reamer, a distal end of the stop element being configured to contact a proximal end of a distal reamer insertable into the distal opening of the proximal reamer; wherein the stop element is switchable between an unlocked state, in which the stop element is longitudinally positionable with respect to the proximal reamer, and a locked state, in which the stop element is locked to the proximal reamer at one of a plurality of discrete, specified longitudinal locations along the proximal reamer.

In Example 2, the adjustable reaming device of Example 1 can optionally be configured such that the proximal reamer further defines a first longitudinal slot and a first plurality of enlarged aperture regions along the first longitudinal slot; and the stop element includes a first prong biased to extend radially outward from within the proximal reamer, a first portion of the first prong being sized larger than a circumferential diameter of the first longitudinal slot and smaller than the enlarged aperture regions in the first plurality.

In Example 3, the adjustable reaming device of Example 2 can optionally be configured such that when the stop element switches from the unlocked state to the locked state, the first portion of the first prong snaps into one of the enlarged aperture regions in the first plurality, thereby locking the stop element to the proximal reamer.

In Example 4, the adjustable reaming device of Example 3 can optionally further comprise a first button disposed on the first prong and configured to transmit radially-inward force to the first prong, so that when the stop element is locked to the proximal reamer, the radially-inward force radially compresses the stop element, thereby unlocking the stop element from the proximal reamer.

In Example 5, the adjustable reaming device of Example 4 can optionally be configured such that when the stop element is in the unlocked state, an applied longitudinal force on the first button longitudinally translates the stop element with respect to the proximal reamer.

In Example 6, the adjustable reaming device of one of Examples 1-5 can optionally be configured such that the proximal reamer further defines first and second longitudinal slots on opposite sides of the proximal reamer; the proximal reamer further defines first and second pluralities of enlarged aperture regions along the first and second longitudinal slots, respectively, each enlarged aperture region in the first plurality being positioned at the same location as a corresponding enlarged aperture region in the second plurality; and the stop element includes first and second prongs biased to extend radially outward in opposite directions from within the proximal reamer, a first portion of the first prong being sized larger than a circumferential diameter of the first longitudinal slot and smaller than the enlarged aperture regions in the first plurality, a first portion of the second prong being sized larger than a circumferential diameter of the second longitudinal slot and smaller than the enlarged aperture regions in the second plurality.

In Example 7, the adjustable reaming device of Example 6 can optionally be configured such that when the stop element switches from the unlocked state to the locked state, the first portions of the first and second prongs snap into corresponding enlarged aperture regions in the first and second pluralities, thereby locking the stop element to the proximal reamer.

In Example 8, the adjustable reaming device of Example 7 can optionally further comprise first and second buttons disposed on the first and second prongs, respectively, and configured to transmit radially-inward force to the first and second prongs, so that when the stop element is locked to the proximal reamer, the radially-inward force radially compresses the stop element, thereby unlocking the stop element from the proximal reamer.

In Example 9, the adjustable reaming device of Example 8 can optionally be configured such that when the stop element is in the unlocked state, applied longitudinal forces on the first and second buttons longitudinally translate the stop element with respect to the proximal reamer.

In Example 10, the adjustable reaming device of Example 9 can optionally be configured such that the stop element is U-shaped; a bottom of the U-shape is configured to abut the distal reamer; and a top of the U-shape includes the first and second prongs.

In Example 11, the adjustable reaming device of one of Examples 1-10 can optionally further comprise a reamer quick-connection positioned on a proximal end of the proximal reamer.

In Example 12, the adjustable reaming device of one of Examples 1-11 can optionally further comprise a longitudinally-elongated distal reamer insertable into the distal opening of the proximal reamer, the distal reamer being rotationally uncoupled from the proximal reamer; wherein the stop element limits longitudinal motion of the proximal reamer in the distal direction, with respect to the distal reamer, but not in the proximal direction, with respect to the distal reamer.

In Example 13, an adjustable reaming device can comprise a longitudinally-elongated proximal reamer, a distal end of the proximal reamer defining a distal opening into an interior of the proximal reamer, the distal end of the proximal reamer including at least one cutting flute surrounding the distal opening; and a driver disposed within the interior of the proximal reamer, a distal end of the driver being configured to contact a proximal end of a distal reamer insertable into the distal opening of the proximal reamer; wherein the driver is switchable between an unlocked state, in which the driver is longitudinally positionable with respect to the proximal reamer, and a locked state, in which the driver is locked to the proximal reamer at one of a plurality of discrete, specified longitudinal locations along the proximal reamer.

In Example 14, the adjustable reaming device of Example 13 can optionally be configured such that the proximal reamer defines a longitudinal slot and a plurality of circumferential slots, each circumferential slot in the plurality having a first end that is connected to the longitudinal slot, each circumferential slot in the plurality having a second end that includes a spring mechanism.

In Example 15, the adjustable reaming device of Example 14 can optionally be configured such that the driver includes a prong extending radially outward from within the proximal reamer, the prong being sized to fit within the longitudinal slot and the circumferential slots in the plurality.

In Example 16, the adjustable reaming device of Example 15 can optionally be configured such that when the driver switches from the unlocked state to the locked state, the driver is positioned longitudinally so that the prong aligns with one of the circumferential slots, then the driver is rotated about a longitudinal axis so that the prong traverses the circumferential slot and engages the spring mechanism.

In Example 17, the adjustable reaming device of one of Examples 13-16 can optionally further comprise a reamer quick-connection positioned on a proximal end of the driver.

In Example 18, the adjustable reaming device of one of Examples 13-17 can optionally further comprise a longitudinally-elongated distal reamer insertable into the distal opening of the proximal reamer, the distal reamer being rotationally uncoupled from the proximal reamer; wherein the driver limits longitudinal motion of the proximal reamer in the distal direction, with respect to the distal reamer, but not in the proximal direction, with respect to the distal reamer.

In Example 19, a method for adjusting a reaming device can comprise providing a longitudinally-elongated proximal reamer, a distal end of the proximal reamer defining a distal opening into an interior of the proximal reamer; positioning a positionable element longitudinally within the proximal reamer, a distal end of the positionable element being configured to abut a distal reamer insertable into the distal opening, thereby limiting longitudinal motion of the proximal reamer in the distal direction, with respect to the distal reamer, but not in the proximal direction, with respect to the distal reamer; and locking the positionable element to the proximal reamer at one of a plurality of discrete, specified longitudinal locations along the proximal reamer.

In Example 20, the method of Example 19 can optionally further comprise unlocking the positionable element from the proximal reamer; repositioning the positionable element longitudinally within the proximal reamer to another of the discrete, specified longitudinal locations in the plurality; and locking the positionable element to the proximal reamer.

In Example 21, the adjustable reaming device or method of any one or any combination of Examples 1-20 can optionally be configured such that all elements, operations, or other options recited are available to use or select from.

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown or described. However, the inventors also contemplate examples in which only those elements shown or described are provided. Moreover, the inventors also contemplate examples using any combination or permutation of those elements shown or described (or one or more aspects thereof), either with respect to a particular example (or one or more aspects thereof), or with respect to other examples (or one or more aspects thereof) shown or described herein. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, kit, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An adjustable reaming device, comprising:
a longitudinally-elongated proximal reamer, a distal end of the proximal reamer defining a distal opening into an interior of the proximal reamer, the distal end of the proximal reamer including at least one cutting flute surrounding the distal opening; and
a stop element disposed within the interior of the proximal reamer, a distal end of the stop element being configured to contact a proximal end of a distal reamer insertable into the distal opening of the proximal reamer;
wherein the stop element is switchable between an unlocked state, in which the stop element is longitudinally positionable with respect to the proximal reamer, and a locked state, in which the stop element is locked to the proximal reamer at one of a plurality of discrete, specified longitudinal locations along the proximal reamer.

2. The adjustable reaming device of claim 1,
wherein the proximal reamer further defines a first longitudinal slot and a first plurality of enlarged aperture regions along the first longitudinal slot; and
wherein the stop element includes a first prong biased to extend radially outward from within the proximal reamer, a first portion of the first prong being sized larger than a circumferential diameter of the first longitudinal slot and smaller than the enlarged aperture regions in the first plurality.

3. The adjustable reaming device of claim 2, wherein when the stop element switches from the unlocked state to the locked state, the first portion of the first prong snaps into one of the enlarged aperture regions in the first plurality, thereby locking the stop element to the proximal reamer.

4. The adjustable reaming device of claim 3, further comprising:
a first button disposed on the first prong and configured to transmit radially-inward force to the first prong, so that when the stop element is locked to the proximal reamer, the radially-inward force radially compresses the stop element, thereby unlocking the stop element from the proximal reamer.

5. The adjustable reaming device of claim 4, wherein when the stop element is in the unlocked state, an applied longitudinal force on the first button longitudinally translates the stop element with respect to the proximal reamer.

6. The adjustable reaming device of claim 1,
wherein the proximal reamer further defines first and second longitudinal slots on opposite sides of the proximal reamer;
wherein the proximal reamer further defines first and second pluralities of enlarged aperture regions along the first and second longitudinal slots, respectively, each enlarged aperture region in the first plurality being positioned at the same location as a corresponding enlarged aperture region in the second plurality; and
wherein the stop element includes first and second prongs biased to extend radially outward in opposite directions from within the proximal reamer, a first portion of the first prong being sized larger than a circumferential diameter of the first longitudinal slot and smaller than the enlarged aperture regions in the first plurality, a first portion of the second prong being sized larger than a circumferential diameter of the second longitudinal slot and smaller than the enlarged aperture regions in the second plurality.

7. The adjustable reaming device of claim 6, wherein when the stop element switches from the unlocked state to the locked state, the first portions of the first and second prongs snap into corresponding enlarged aperture regions in the first and second pluralities, thereby locking the stop element to the proximal reamer.

8. The adjustable reaming device of claim 7, further comprising:
first and second buttons disposed on the first and second prongs, respectively, and configured to transmit radially-inward force to the first and second prongs, so that when the stop element is locked to the proximal reamer, the radially-inward force radially compresses the stop element, thereby unlocking the stop element from the proximal reamer.

9. The adjustable reaming device of claim 8, wherein when the stop element is in the unlocked state, applied longitudinal forces on the first and second buttons longitudinally translate the stop element with respect to the proximal reamer.

10. The adjustable reaming device of claim 9,
wherein the stop element is U-shaped;
wherein a bottom of the U-shape is configured to abut the distal reamer; and wherein a top of the U-shape includes the first and second prongs.

11. The adjustable reaming device of claim 1, further comprising a reamer quick-connection positioned on a proximal end of the proximal reamer.

12. The adjustable reaming device of claim 1, further comprising:
   a longitudinally-elongated distal reamer insertable into the distal opening of the proximal reamer, the distal reamer being rotationally uncoupled from the proximal reamer;
   wherein the stop element limits longitudinal motion of the proximal reamer in the distal direction, with respect to the distal reamer, but not in the proximal direction, with respect to the distal reamer.

* * * * *